United States Patent [19]

Lindén

[11] Patent Number: 4,882,867
[45] Date of Patent: Nov. 28, 1989

[54] DENTAL INSTRUMENT HAVING IDENTIFICATION MARKINGS

[76] Inventor: Sigurd R. Lindén, Teatergatan 4, S-582 22 Linköping, Sweden

[21] Appl. No.: 228,914
[22] PCT Filed: Mar. 6, 1987
[86] PCT No.: PCT/SE87/00114
  § 371 Date: Aug. 3, 1988
  § 102(e) Date: Aug. 3, 1988
[87] PCT Pub. No.: WO87/05487
  PCT Pub. Date: Sep. 24, 1987

[30] Foreign Application Priority Data

Mar. 13, 1986 [SE] Sweden .............................. 8601188

[51] Int. Cl.⁴ .............................................. G09F 3/02
[52] U.S. Cl. ...................................... 40/625; 40/913; 264/271.1
[58] Field of Search ............... 433/141, 102; 40/625, 40/628, 913, 915, 629, 317, 334; 264/271.1, 273, 274

[56] References Cited

U.S. PATENT DOCUMENTS 1,984,839 12/1934 Murray .............................. 283/74
2,016,644 10/1935 Luball ............................... 40/628
2,915,926 12/1959 Woerner .......................... 40/913
4,671,916 6/1987 Hamas ............................. 40/913
4,720,907 1/1988 Rapp ................................ 40/628

Primary Examiner—Gene Mancene
Assistant Examiner—Cary E. Stone
Attorney, Agent, or Firm—Sughrue, Mion, Zinn, Macpeak and Seas

[57] ABSTRACT

A dental instrument of the type comprising an elongate handle portion (1) which consists of a plastic material and which, at least at its one end, has an instrument portion (2,3). In its circumferential surface it has annular, differently colored zones (4,5) which facilitate identification of a desired instrument in the way that different functions correspond to annular zones in different numbers and/or in different colors. The invention solves the problem of providing such an instrument having an essentially unlimited usefull life as far as the colored marking is concerned. This has been achieved in the way that each annular zone (4,5) is constituted by the circumferential surface of a member (7) shaped like a ring, a sleeve, or disc which is mounted on a shaft-like extension(6) of the instrument portion inside the handle portion (1) and between the ends thereof.

4 Claims, 1 Drawing Sheet

DENTAL INSTRUMENT HAVING IDENTIFICATION MARKINGS

The present invention relates to a dental instrument of the type comprising an elongate handle portion, which consists of a plastic material and which, at least at its one end, has an instrument portion. Further, said handle has circumferential mutually different, ring zones for the purpose of facilitating identification of an instrument to be selected by the dentist. Generally, instruments having different functions exhibit such zones present in different numbers and/or in different colours.

The development of odontology which has taken place during the latest decades has resulted in a significant increase of the number of technical equipment which dentists have to use when treating patients. This is especially true in respect of hand instruments of the type above mentioned. Not only has the number of different instruments increased due to the fact that different functions require different instruments but, in addition thereto, each such function requires a group of instruments differing from each other in respect of the size, shape etc. of the tool parts proper. As a matter of fact, the total number of such instruments is now that great that it has become common practice to collect each functional group of instruments on a prepared tray, e.g. amalgam trays, deturation trays etc. In order to make it possible for the dentist quickly to distinguish between different instrument groups on such a tray the handle portions within each such group have a common colour which may be obtained by e.g. an eloxation process. However, there does then still remain the problem of quickly and conveniently differentiate the various instruments inside each group. This can be achieved in the way that the handle portions are provided with circumferential markings in colours deviating from the colour of the handle body. It has been suggested to apply the colours by painting. However, this method is most unsatisfactory since the instruments must stand sterilization, e.g. in a autoclave. During such sterilization processes the instruments are subjected to high temperatures and/or to the influence of chemically active substances causing the applied ring markings to weaken and, eventually, to disappear completely after a period of time which is unacceptably short from an economical point of view.

The object of the invention is to provide a dental instrument of the type above defined in which the identifying circumferential zones get a long effective lifetime. According to the generic inventive idea this has been achieved in the way that each identifying ring zone is constituted by the envelope surface of an annular, sleeve- or disc-like member carried by a tool portion extending axially inside the handle. This means that the ring zones will be constituted by three-dimensional bodies and not by thin, two-dimensional layers.

The invention does also relate to a method of manufacturing such a dental instrument. The new method comprises the steps of first applying onto a portion of the instrument, which in the completed instrument is surrounded by the handle, one or more members shaped like rings, sleeves or discs, and then forming said handle, preferably by moulding or injection-moulding it from a plastic material, the colour of which differs from the colour of each individual ring zone.

One embodiment of the invention will now be described with reference to the drawing.

Figure 1:
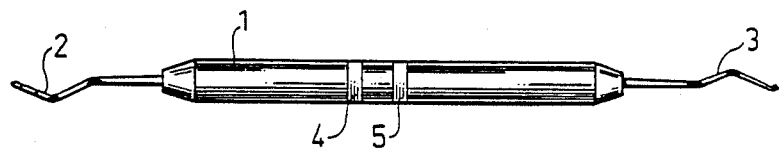
FIG. 1 is a lateral view of a completed dental instrument having two marking rings.

The instrument shown in FIG. 1 has a handle portion shaped like an elongate sleeve 1 and, at each of its two ends, an instrument, or tool, portion 2 and 3, respectively. In order to mark the function of the instrument its handle has been provided with two ring zones 4 and 5 in a colour different from that of the main portion of the handle. Rings 4 and 5 may either have the same colour, in which case the detailed function of the instrument inside the group to which it belongs appears from the number of such rings or, alternatively, each ring zone may have a colour of its own, then suitably symbolizing the function of its adjacent tool portion. It is also possible to combine those two identification systems. According to the prior art ring zones 4 and 5 were applied as thin layers and tool portions 2 and 3 were separate units which, during the manufacturing process were inserted into bores in the handle portion 1 and there in some suitable manner secured against rotation.

Figure 2:
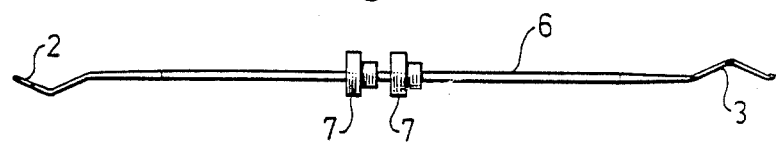
FIG. 2 is a lateral view illustrating a stage of the manufacturing process.

An instrument according to the present invention differs from the prior art in both those respects which appears from FIG. 2. Tool shaft 6 extends a long distance into handle 1 and when, as is the case in the embodiment illustrated, the handle carries two tool parts, shaft 6 is integral with both tools. The second difference is that the ring zones are not constituted by thin, painted layers but are formed by the envelope surfaces of three-dimensional sleeve-like members 7. As appears from FIG. 2, these members are mounted on shaft 6 before the formation of handle 1.

Figure 3:
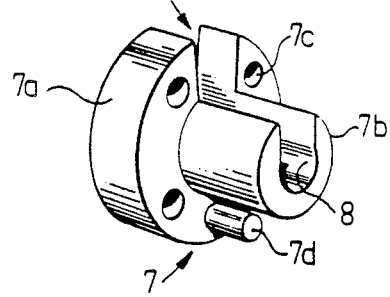
FIG. 3 is a perspective view showing a circular member the envelope surface of which will constitute an identifying zone of the instrument handle.

FIG. 3 does in a perspective view show a sleeve-like member 7 according to the illustrated embodiment of the invention. It appears from FIG. 3 that member 7 has two main portions, a portion 7a shaped like a disc or a washer and having an outer diameter substantially agreeing with that of the handle, and a sleeve-like portion 7b having a considerably smaller outer diameter. Member 7 is traversed by an axial bore 8 the diameter of which corresponds to that of shaft 6. However, bore 8 is not completely closed in its circumferential direction but exhibits a radial slot 9 the task of which is to make it possible to mount the member on shaft 6 by displacement in a radial direction. Bore 8 and slot 9 are preferably dimensioned in such a way that member 7 will be retained on shaft o by a snapping action. Suitably, member 7 consists of a plastic material but also other materials, such as metals, can be used.

When the desired number of cylindrical members 7 have been mounted on shaft 6, the body portion of handle 1 is formed, suitably by a moulding or injection-moulding process. The last-mentioned manufacturing alternative has been diagrammatically illustrated in FIG. 4. Reference numeral 10 designates the injector proper having its hopper 11 and its stoker 12. Via a pipe 13 it communicates with the internal space of a mould 14 having an upper and a lower half. The lower half is vertically movable by means of a linkage mechanism 15 controlled by a piston-cylinder unit 16. Injection-moulding machine 10-16 does not constitute any part of the present invention but may be of any known or suitable configuration. The equipment has been shown only for the purpose of illustrating a preferred mode of working the invention.

Figure 4:
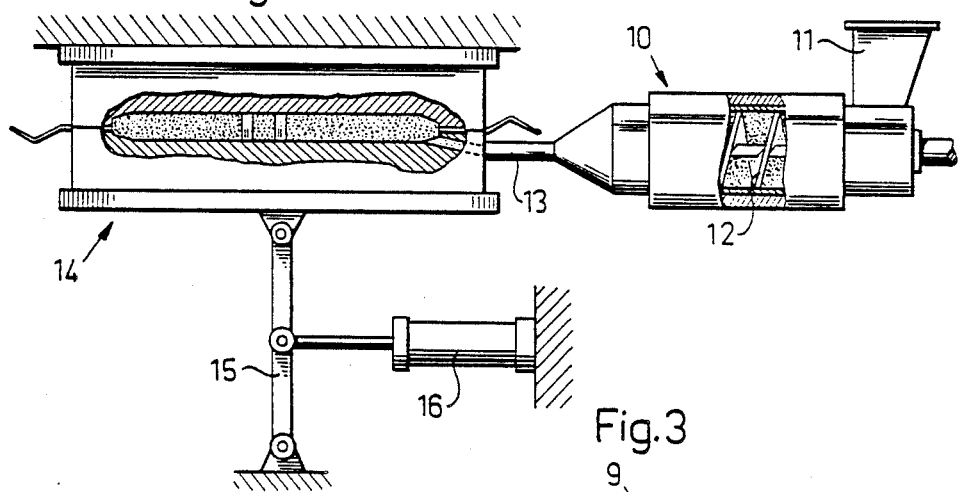
FIG. 4 is a part-sectional, diagrammatic, lateral view of a device for injection-moulding of the handle of the instrument in conformity with the method according to the invention.

As shown in FIG. 4 the last manufacturing step is to form the handle body 1 by injecting a plastic material into the mould through pipe 13. In order to facilitate the passage of the plastic material past members 7 they have been provided with through bores 7c augmenting the passage area formed by slot 9. However, bores 7c have another function as well, namely in the completed instrument shown in FIG. 1. This function is obtained thanks to the fact that the plastic material in handle body 1 does axially extend through bores 7c thereby fixing in a radial direction the position of each member 7. The purpose of this retaining action is to prevent the securing force generated by said snapping action to disappear due to tensions inside the material which may be generated at elevated temperatures in connection with sterilization and which might generate a radially directed force that could expel member 7 from shaft 6, at least in the absence of the sleeve-like extension 7b. According to the example illustrated in FIG. 3 member 7 also has an axial pin 7d preventing rotation of member 7.

The description above discloses both the structural nature of the instrument and a method of manufacturing it. As is understood, the inventive idea consists in the realization that the drawbacks and limitations of the prior art instruments referred to above are eliminated in the way that painted or otherwise applied, thin layers are replaced by three-dimensional bodies. It follows therefrom that the invention may be varied in many ways as far as the structural and functional details are concerned. By way of example, it can be mentioned that bores 7c do not have to extend through disc 7a but may simply be axial depressions. However, as has been explained above, use of through-bores does on the other hand facilitate the passage of the plastic material during the moulding process.

I claim:

1. A dental instrument of the type comprising an elongate handle portion (1) which consists of a plastic material and which, at least at its one end, has an instrument (2, 3), the circumferential surface of the handle portion exhibiting annular zones (4, 5) which are of mutually different colours for the purpose of facilitating identification of an instrument to be selected by the dentist, namely in the way that instruments having different functions comprise annular zones in different numbers and/or in different colours, characterized in that each annular zone (4, 5) is constituted by the circumferential surface of a member (7) having a shape selected from the group comprising a ring, a sleeve and a disc, and is supported by a shaft-like extension (6) of the instrument portion extending inside the handle portion between the two ends thereof.

2. A dental instrument as claimed in claim 1, characterized in that members (7) are retained on the shaft (6) of the instrument portion by a snapping action.

3. A dental instrument as claimed in claim 1 or 2, characterized in that, in order to keep members (7) safely secured, especially against radially directed forces generated by tensions arising inside said members when exposed to elevated temperature in connection with sterilization, each of members (7) has a number of recesses in their end surfaces, preferably in the form of axial through-holes (7c), adapted to receive the plastic material of the handle portion (1).

4. A method of manufacturing a dental instrument of the type comprising an elongate handle portion (1) which consists of a plastic material and which, at least at its one end, has an instrument portion (2, 3), and, in its circumferential surface, annular zones (4, 5) of different colours for the purpose of facilitating identification of an instrument to be selected by the dentist, instruments for different functions having annular zones in different numbers and/or in different colours, characterized by the steps of mounting on a section (6) of the instrument portion, which section is in the completed instrument surrounded by said handle portion, a number of members (7) having shapes selected from the group comprising rings, sleeves and discs, forming said handle portion, preferably by injection-moulding or moulding of a plastic material the colour of which is different from the colour of each annular zone (4, 5).

* * * * *